United States Patent [19]

Sciaraffa et al.

[11] 4,333,979
[45] Jun. 8, 1982

[54] SOFT, BULKY, LIGHTWEIGHT NONWOVEN WEB AND METHOD OF PRODUCING; THE WEB HAS BOTH FUSED SPOT BONDS AND PATTERNED EMBOSSMENTS

[75] Inventors: Michael A. Sciaraffa; David G. Thome, both of Appleton; Clifford M. Vogt, Neenah, all of Wis.

[73] Assignee: Kimberly-Clark Corporation, Neenah, Wis.

[21] Appl. No.: 179,054

[22] Filed: Aug. 18, 1980

[51] Int. Cl.³ ............... A61F 13/16; D04H 3/14; D04H 5/06
[52] U.S. Cl. ............... 428/179; 128/290 W; 156/181; 156/209; 156/308.4; 428/180; 428/182; 428/183; 428/198; 428/283; 428/288; 428/296; 428/337; 428/340
[58] Field of Search ......... 428/198, 296, 337, 340, 428/288, 179, 180, 182, 183, 283; 128/290 W; 156/181, 306, 209; 19/296

[56] References Cited

U.S. PATENT DOCUMENTS

| | | | |
|---|---|---|---|
| D. 239,566 | 4/1976 | Vogt | D59/2 |
| 3,616,157 | 10/1971 | Smith | 161/124 |
| 3,774,610 | 11/1973 | Eckert et al. | 128/287 |
| 3,814,101 | 6/1974 | Kozak | 128/287 |
| 3,848,595 | 11/1974 | Endres | 128/284 |
| 3,855,046 | 12/1974 | Hansen et al. | 161/150 |
| 4,041,951 | 8/1977 | Sanford | 128/287 |
| 4,050,462 | 9/1977 | Woon et al. | 128/287 |
| 4,259,390 | 3/1981 | Fahrbach et al. | 428/198 |
| 4,265,954 | 5/1981 | Romonck | 428/296 |

FOREIGN PATENT DOCUMENTS

820104  8/1969  Canada .................... 28/78

*Primary Examiner*—James C. Cannon
*Attorney, Agent, or Firm*—William D. Herrick; Howard Olevsky

[57] ABSTRACT

Lightweight, pattern bonded, generally continuous filament web having physical, aesthetic, and functional attributes particularly desirable for liner material for disposable absorbent products such as diapers, sanitary napkins, and the like. In accordance with a preferred embodiment of the invention, a continuous filament polypropylene web is formed and pattern bonded by heat and pressure producing a high frequency of high density bond areas. This bonded web is then subjected to hot embossing in a gross pattern producing permanent web deformation and increasing the web effective thickness. In use the nonwoven web of the invention provides a very soft, flexible web having a pleasing appearance and yet retaining strength properties making it very effective at low basis weights for applications such as liners for disposable diapers, sanitary napkins, and the like. The method of the invention includes melt spinning and accumulating the spun fibers into a web that is pattern bonded in a fine pattern by heat and pressure and then subjected to a gross pattern of embossments under heated conditions.

15 Claims, 11 Drawing Figures

SOFT, BULKY, LIGHTWEIGHT NONWOVEN WEB AND METHOD OF PRODUCING; THE WEB HAS BOTH FUSED SPOT BONDS AND PATTERNED EMBOSSMENTS

CROSS REFERENCE TO RELATED APPLICATIONS

An embossing pattern useful in the present invention is disclosed in copending design patent application Ser. No. 148,973, filed May 12, 1980, by Sciaraffa and Thome and entitled "Pattern Design for Lightweight Fabric".

BACKGROUND OF THE INVENTION

1. Field of the Invention

This invention relates to nonwoven webs of thermoplastic fibers and their manufacture. More particularly, the invention relates to lightweight nonwoven webs having attributes of softness, strength and appearance especially suitable for applications such as disposable diaper liners, wrappers for sanitary napkins, and the like. Such webs may be formed by melting a thermoplastic material and spinning it to form filaments or fibers which are collected and interbonded at desired basis weights. To be useful for the identified applications as well as others, the web is desirably sufficiently porous to allow waste material deposited on the product, for example, a disposable diaper to pass through and yet strong enough to prevent disintegration of the web. In addition, the web should be attractive in appearance and sufficiently opaque to cover discoloration and the like. Finally, for comfort the web should be soft and flexible as well as nonirritating.

2. Description of the Prior Art

Nonwoven materials of the type generally described have been available for years and have been the subject of intensive investigation, particularly since the development and widespread use of disposable diapers. It is known, and conventional, for example, to utilize spunbonded polymeric filament webs in the basis weight of about 1 oz/yd$^2$ or less as a liner for disposable diapers. Further, other materials such as bonded carded webs, fibrillated films, and scrimlike materials of low basis weight have been so used. It is also known that some appearance and functional aspects of nonwoven diaper liners can be improved by embossing the web to produce more or less permanent deformation.

Examples of such disclosures include U.S. Pat. No. 4,041,951 to Sanford, U.S. Pat. No. 3,616,157 to Smith, Canadian Pat. No. 820,104 to Paulig and Taylor, U.S. Pat. No. 3,814,101 to Kozak, and U.S. Pat. No. 4,050,462 to Woon and Endres.

In general, however, selection of a nonwoven facing material has involved a compromise between desirable physical and functional attributes and comfort and appearance factors. Furthermore, cost considerations have fostered a tendency to seek lighter basis weight materials. Consequently a need has been demonstrated for a light basis weight nonwoven facing material having adequate strength and having softness and bulk without deterioration of desirable physical properties.

SUMMARY

The present invention provides a lightweight nonwoven web formed from continuous thermoplastic filaments substantially randomly oriented and pattern bonded, but further embossed under heat and pressure conditions resulting in an increased effective thickness providing softness and bulk while retaining other desirable physical properties such as strength. The materials of the invention are highly effective as liners for disposable products such as diapers, sanitary napkins, and the like at very light basis weights. Accordingly, an economic material is obtained without the sacrifices usually attendant such economies in the materials of the prior art.

In accordance with the invention the spunbonded pattern is composed of closely spaced point fused areas, while the subsequently applied embossing pattern comprises a gross pattern of much larger overall embossments. The embossing depth and pattern are selected to result in a web cross section of greatly increased thickness. The combination of the close spot bonds and overall gross embossments provide softness and bulk while retaining significant strength properties.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications and equivalents as may be included in the spirit and scope of the invention as defined by the appended claims.

In general, the present invention provides improvements in spunbonded lightweight thermoplastic webs. A wide variety of thermoplastic materials may be employed so long as the resulting web is capable of spot-bonding and embossing to provide a substantially permanently deformed structure. Examples include polyolefins such as polyethylene and polypropylene, polyesters such as polyethylene terephthalate and polyamides such as nylon. Under some circumstances other materials not normally classed as thermoplastics may be utilized as well such as glass filaments, for example. Any of these materials may be employed alone or in admixture or as multicomponent composite compositions. In some cases it may be desirable to include up to 5%, preferably up to 2% by weight of a filler material for economy and other purposes. Such fillers may include, for example, clays and titanium dioxide. In a particularly preferred embodiment up to 70% especially up to 30% by weight of cellulose wood fibers are included for further enhanced tactile and performance properties.

The web as formed is preferably composed of generally continuous filaments, but may be formed from textile length or even shorter fibers if desired. The filament length may affect the pattern bonding step since it will be desired to have the bond pattern spacing not exceeding a fiber length between bond areas. For continuous filament webs, however, the bond pattern is preferably as generally described in U.S. Pat. No. 3,855,046 to Hansen and Pennings, which is incorporated herein by reference or as illustrated in U.S. Design Pat. No. 239,566 to Vogt. As described in U.S. Pat. No. 3,855,046, continuous filament webs are formed by extrusion and drawing through a take-off device. The drawn filaments are deposited in a substantially random manner on a moving carrier through air guns. The filaments form loops and swirls which overlap and result in intermingling of filaments forming a substantially random and uniform nonwoven web. Bonding of the web is achieved without the application of independently applied adhesives or solvents by passing the web through a pattern nip formed by heated rolls. Individual compacted fused areas are formed occupying about 5 to 50% of the total web area and with a density of about 50 to 3200 fused areas per square inch. The spunbonded web, thus, contains a pattern of high density fused bond areas and relatively low density, unbonded areas.

In accordance with the present invention, such pattern bonded nonwoven webs are further processed by applying a gross embossing pattern imparting a substantially permanent deformation in the form of a pattern of depressed areas. This gross pattern embossment is preferably obtained by passing the pattern bonded web through a nip formed by a matched set of heated steel embossing rolls. As shown in detail with respect to alternative embodiments in FIGS. 8–10, one roll contains a pattern having a depth and configuration selected to produce the desired permanent deformation and the other roll includes a corresponding female pattern. Selection of the pattern is critical to obtain the results of the present invention. The pattern will occupy an area of about 5 to 80% and preferably 5 to 30% of the web surface with embossed pattern frequency in the range of from about 1 to 500, preferably 1 to 100 per square inch. Also in accordance with the invention, the raised portions forming the pattern of the nip are preferably formed with rounded edges and sharp corners are avoided. A further important feature of the present invention is that the shape of the individual embossments is preferably of an oval configuration and arranged in a pattern of biased oval configuration as illustrated in the above-identified Sciaraffa and Thome design patent application Ser. No. 148,973. After embossing, the web is immediately applied to the manufactured product such as disposable diapers or the like. Alternatively, it may be wound and stored for further use, but, in such cases, the web is preferably wound under conditions of low or zero tension to avoid deterioration of the embossed web characteristics. Further, storage of such rolls should be under conditions which would not tend to stretch or press the web.

The lightweight webs of the invention have a basis weight in the range of from 0.4 oz/yd$^2$ to 2.0 oz/yd$^2$, preferably 0.5 oz/yd$^2$ to 1.0 oz/yd$^2$. Web density is in the range of 0.08 to 0.20 g/cc, preferably 0.10 to 0.18 g/cc.

Turning to the drawings, the preferred embodiments will now be described in greater detail.

Figure 1:
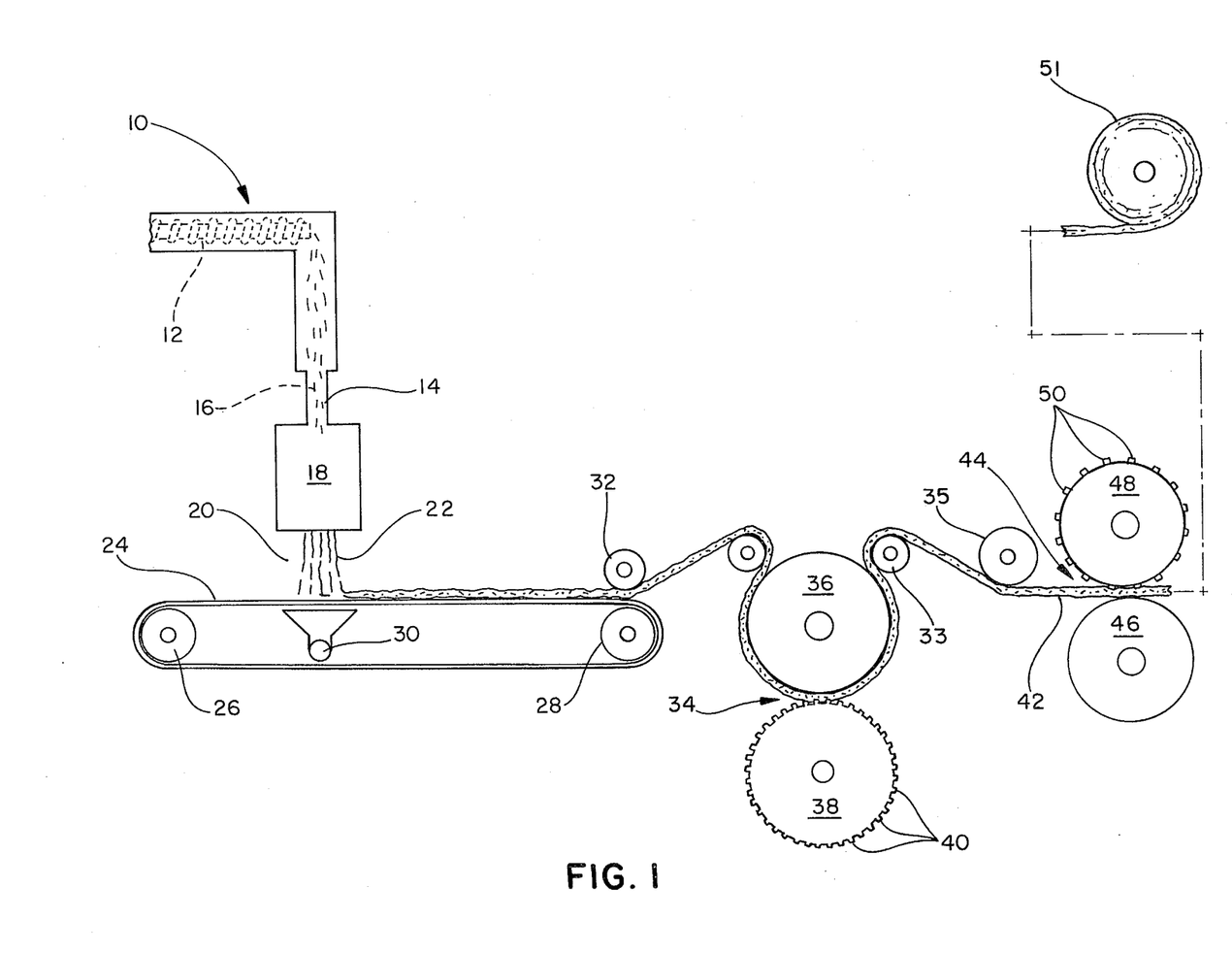
FIG. 1 is a schematic illustration of the process of the present invention.

FIG. 1 illustrates the process of the present invention in schematic form. Extruder 10 causes polymer 12 to become molten at spinnerette 14. Through spinnerette 14 filaments 16 are discharged into quench zone 18 and from there through draw zone 20. Drawn filaments 22 exit and are collected on screen 24 which rotates about rolls 26 and 28. For improved formation, if desired, vacuum 30 may assist filament lay-down. The web is compacted at the nip formed by rolls 32 and 28, and the web is then directed to bonding nip 34 formed by steel rolls 36 and 38. Roll 38 contains a pattern of projections 40, and at least one of rolls 36 and 38 is heated. After bonding at nip 34, the web 43 is fed over guide rolls 33 and 35 to embossing nip 44 formed by rolls 46 and 48. As shown in greater detail in FIGS. 8–10, roll 48 contains projections 50 for embossing and roll 46 a corresponding female pattern. Either or both rolls 46 and 48 can be heated for embossing or the web can be pre-heated and embossed with the rolls at room temperature. After embossing, the web is wound under essentially zero tension into roll 51. As discussed above, if desired, the web may be directed immediately to a converting unit for further processing into disposable products or the like.

Figure 2:
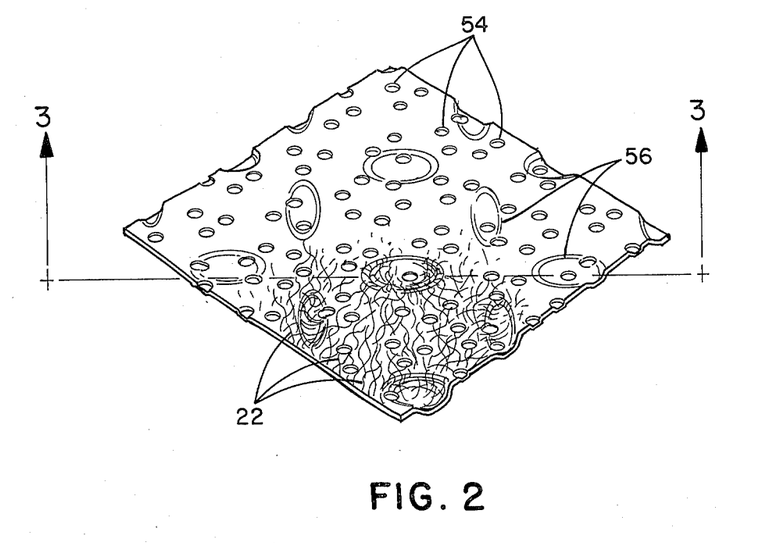
FIG. 2 is a schematic illustration of perspective of a web of the present invention.
Figure 3:
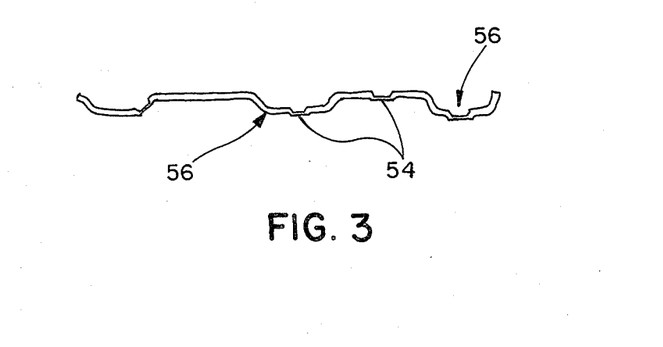
FIG. 3 is a cross section of the web of FIG. 2 taken along lines 3—3 illustrating schematically the increase in bulk attained by the present invention.

Turning to FIG. 2, the web of the invention will be further described. As shown, the web comprises entangled filaments 22 which are integrated at spaced areas by high density, fused bond areas 54. These bonds form a pattern of high frequency and relatively small individual area. Superimposed on the high frequency, high density bond areas 54 is the gross pattern of deep embossments 56. These embossments 56 can be of relatively low or high frequency but generally lower in frequency and larger in individual area than bonds 54 while both are arranged to produce an attractive visual appearance. As shown in FIG. 3, the embossments 56 result in greatly increasing the apparent web thickness by substantially permanent deformation out of the plane of the web.

Figure 4:
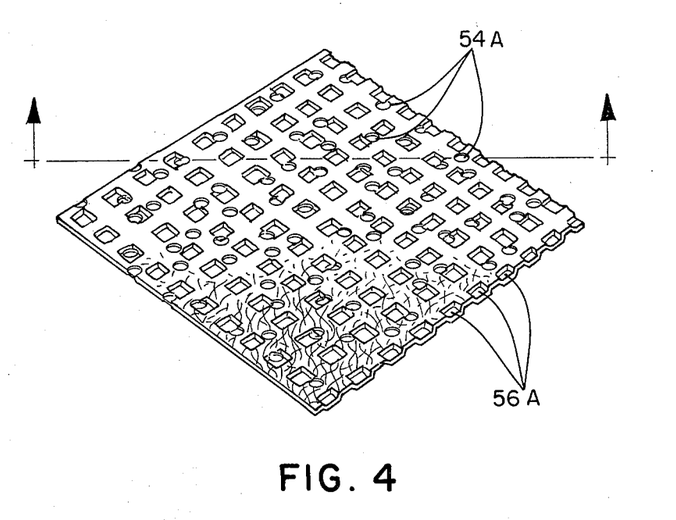
FIGS. 4 and 5 are alternative embodiments illustrated as in FIGS. 2 and 3.
Figure 5:
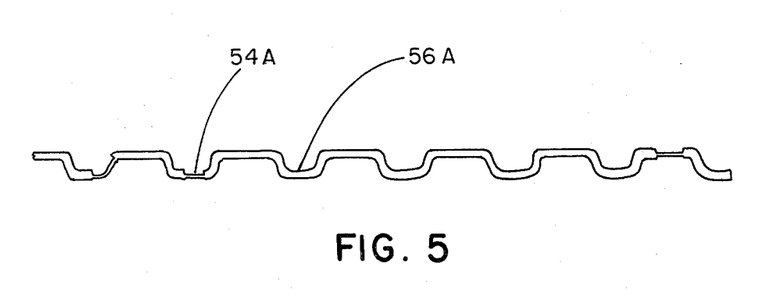

Turning to FIGS. 4 and 5, an alternative pattern of bond areas 54A and gross embossments 56A is illustrated in the manner of FIGS. 2 and 3. In this case a somewhat different visual appearance is presented, but the embossments retain the characteristics of generally rounded configuration.

Figure 8:
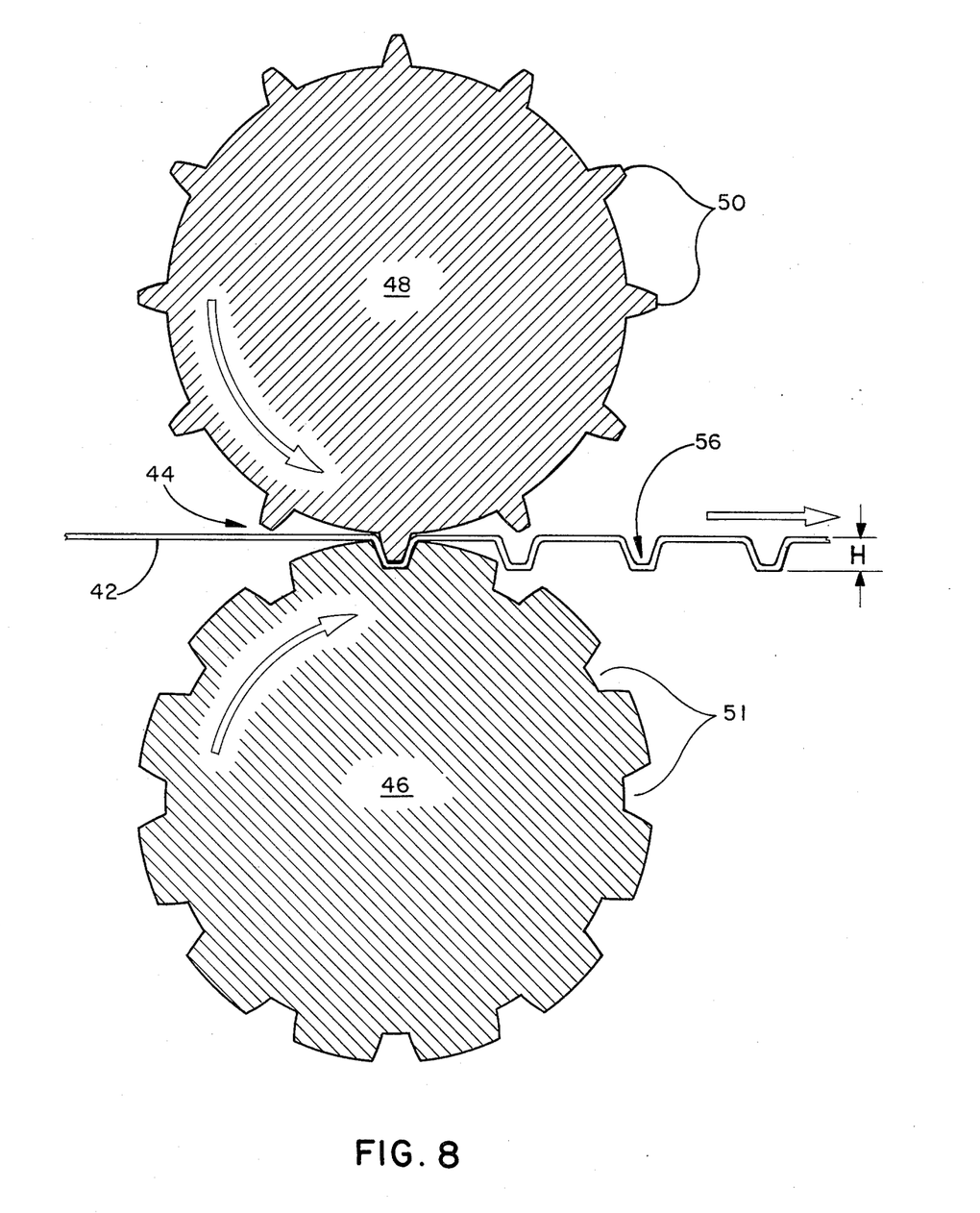
FIGS. 8–10 illustrates the embossing step in greater detail.
Figure 9:
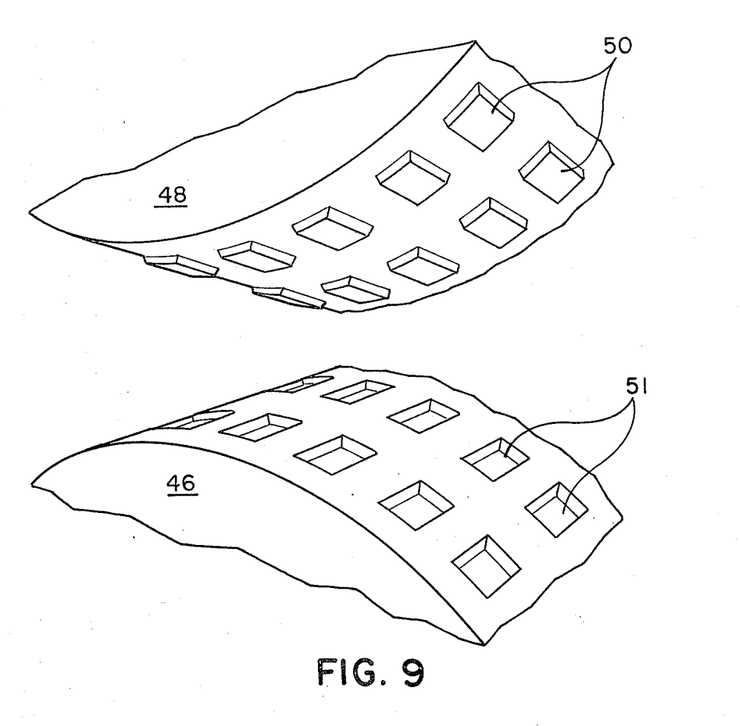
Figure 10:
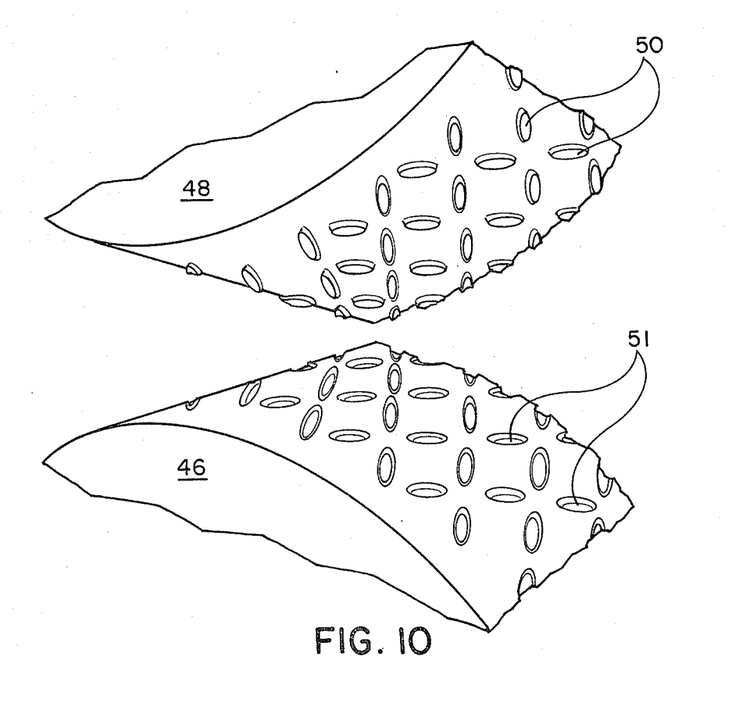

Turning to FIGS. 8–10 the embossing nip 44 is illustrated in greater detail. As shown, the projections 50 on roll 48 are preferably formed without sharp corners and match impressions 51 in roll 46, thus subjecting the web (bond areas omitted for clarity) to less tearing action during embossing and resulting in improved strength properties with the preferred embodiment of the invention.

While the process and web of the present invention may utilize a wide variety of thermoplastic materials used alone or in combination, preferred compositions include polyolefins including polyethylene and polypropylene, polyesters, including polyethylene terephthalate, polyamides, including nylon as well as composites of these thermoplastics with cellulose fibers. Such thermoplastic materials are capable of being melt-spun and collected as filaments into a web which is capable of bonding and substantially permanent deformation as described. The processing conditions will, of course, vary depending upon the selected material. Generally, however, bonding conditions will involve temperatures in the range of 275° F. to 350° F., pressures generally 3,000 to 50,000 lbs/in$^2$ at speeds generally in the range of from 500 to 1500 ft/min. Similarly, embossing conditions will vary but generally will be in the range of from about 125° F. to 325° F. for temperature while the rolls are gapped with shims to provide a separation of 0.002 to 0.010 inch, preferably 0.003 to 0.006 inch at similar speeds.

The patterns for bonding and embossing are important to achieving the results of the present invention. The bonding pattern will preferably consist of a relatively fine pattern of 125 to 325 bonds per square inch, each having an area in the range of from about 0.0005 in$^2$ to 0.0015 in$^2$. In contrast, a preferred gross embossing pattern will be in the range of from 1 to 100 embossments per square inch and have an individual area of from 0.003 to 0.03 square inches per embossment. The individual embossments, in order to achieve the improved results of the present invention will have a height, H, as illustrated on FIG. 8 of at least about 0.030 inch under zero tension. As shown and described, the webs of the present invention provide a particularly useful liner for disposable products at very light basis weights in the range of up to about 1 oz/yd$^2$. This provides significant improvements in economy and, it will be recognized that heavier weights may be utilized if desired.

Depending upon the use contemplated for the material of the invention, it may be desirable to include fillers such as clay, titanium dioxide, cellulose fibers and the like, and the incorporation of such involves steps known in the art. Similarly, the web of the invention may be treated for specific end uses, if desired, by applying known steps imparting water repellency, antistatic, as well as other treatments which will be apparent to those skilled in the art.

EXAMPLES

EXAMPLE 1

A spunbonded, continuous filament polypropylene web was formed generally as described in the above-mentioned Hansen/Pennings U.S. Pat. No. 3,855,046. The polymer was melted in a conventional extruder and spun as continuous filaments through a spinnerette plate. The web was collected at a speed of 1000 ft/min and bonded by hot calendaring with a pattern having 153 bonds per square inch, each having an area of 0.00098 in$^2$. The pattern used was as illustrated in U.S. Design Pat. No. 239,566, incorporated herein by reference. The spunbonded web was then embossed by passing through a heated nip elevating its temperature to 280° F., at a speed of 500 ft/min and with a pattern of embossments of 18 per square inch, individual embossed areas of 0.005 square inch and in a configuration illustrated in above FIG. 2. The resulting material had a basis weight of 0.7 oz/yd$^2$ and effective Ames thickness of 0.039 inches (the Ames method employed a 5 inch square platten and a pressure of 3.5 lbs/ft$^2$). Strength properties of the web included average cross-direction strength of 10 pounds. (As measured by ASTM D-1117.)

EXAMPLE 2

Example 1 was repeated except that the embossing pattern used contained square shaped embossments having a high frequency of 320 per square inch and individual area of 0.0012 square inches.

EXAMPLE 3

Example 1 was repeated with an embossing pattern of diamond shaped embossments having a frequency of 40 per square inch, individual area of 0.0030 square inch and sharp edges.

EXAMPLE 4

Example 1 was repeated with an embossing pattern of oval shaped embossments having a frequency of 40 per square inch, individual area of 0.0045 square inch and rounded edges.

EXAMPLE 5

Example 1 was repeated with an embossing pattern of round shaped embossments of a frequency of 50 per square inch and individual area of 0.0038 in$^2$ and rounded edges.

EXAMPLE 6

For comparative purposes, a sample of liner material was removed from product marketed under the brand name PAMPERS ® quilted stay dry disposable diaper believed to be embossed.

Table 1 identifies tests made of the materials of the above examples with respect to Ames thickness, tensile strength in the cross direction, and softness. Softness was determined by comparison with standard tissue sheets having softness ratings of from 1 (least soft) to 8 (softest). The sheets to be tested were exposed to standard conditions, 73.5±2° F. and 50±5% R.H. for at least one week before testing. Samples were about 9-¼ inches by 8-½ inches (M.D.×C.D.) in size. The standard sheets were placed in a row, and the samples placed between the standard sheets and the individual performing the tests. The samples were compared to the standard sheets by placing the hand on the sheets with fingers spread, the palm base near a corner and thumb and little finger approximately parallel the sample edges. A loose mass was gathered by moving finger tips towards the palm base and thumb tip toward the base of the middle and index fingers. The hand and sample were raised and the mass positioned to feel where the middle and index fingers join the palm. The thumb was then placed on the thicknesses laying across the middle and index fingers, and the mass repeatedly crushed lightly in the palm letting the fingers slide. At the same time the thumb was moved back and forth lightly on the sample thickness between it and the index and middle fingers. Limpness and surface texture were simultaneously evaluated and rated with equal weight for a combined softness value as compared to the standard sheets to the nearest 0.5 rating.

TABLE I

| Example | Ames Thickness (Inches) | CD Grab Tensile (Pounds) | MD Grab Tensile (Pounds) | Softness |
|---|---|---|---|---|
| No. 1 | 0.039 | 11.6 | 9.0 | 8.0 |
| No. 2 | 0.021 | 9.8 | 9.0 | 8.0 |
| No. 3 | 0.024 | 6.7 | 7.8 | — |
| No. 4 | 0.019 | 11.5 | 8.9 | — |
| No. 5 | 0.018 | 10.4 | — | — |
| No. 6 | 0.021 | 11.1 | 3.4 | 4.5 |

Figure 11:
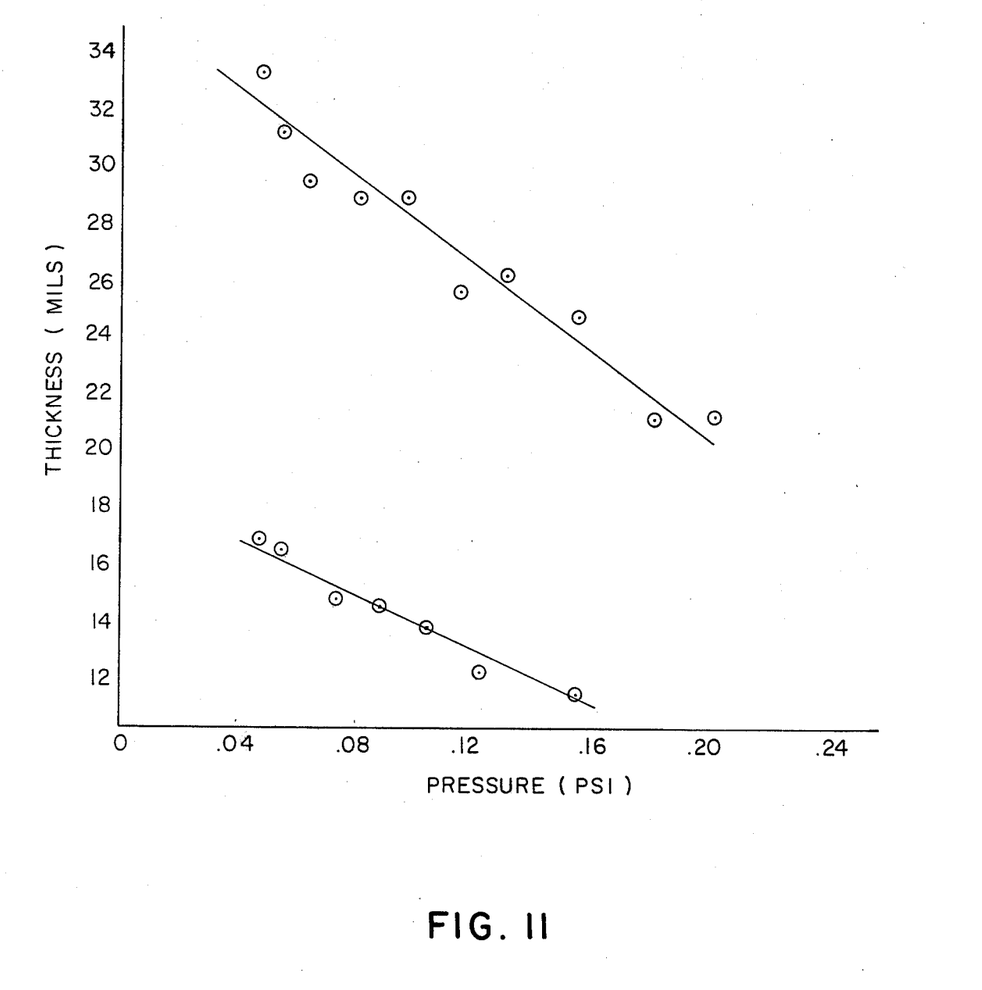
FIG. 11 is a graph illustrating improved results obtained in accordance with the present invention.

FIG. 11 is a graph of bulk measurements taken against pressure measurements comparing the material of Example 1 with the sample embossed diaper liner material. As shown, the process and material of the present invention provides a much bulkier material under pressure conditions which may be experienced in use. While the invention is not to be limited thereto, it is believed that this improvement results from permanent filter deformation during heated embossing.

Figure 6:
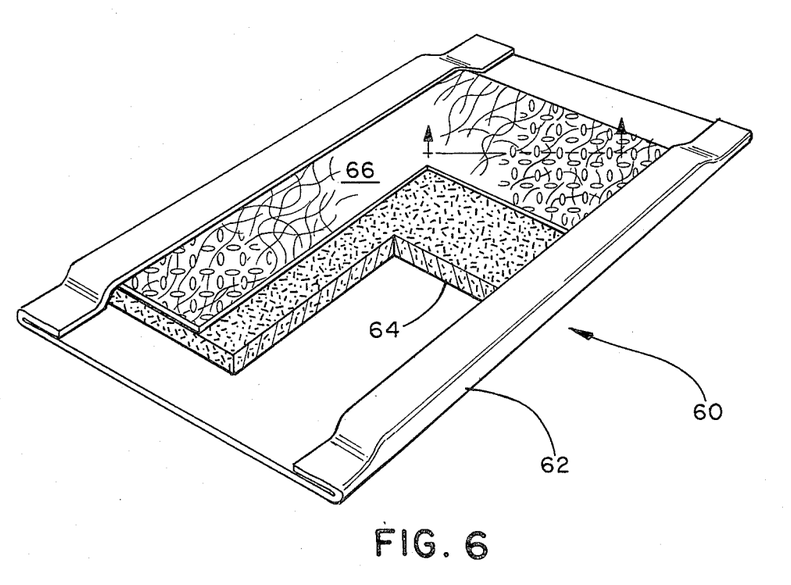
FIG. 6 is a disposable product incorporating the web of the present invention.
Figure 7:
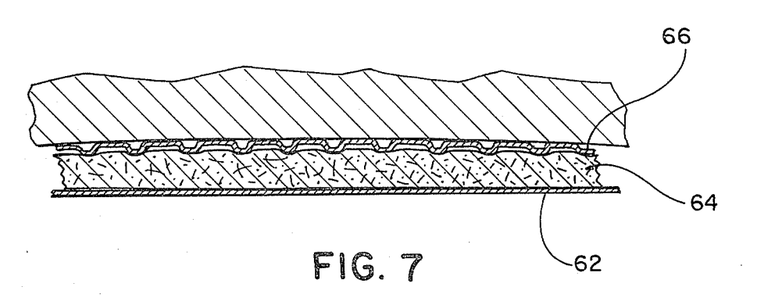
FIG. 7 illustrates the product of FIG. 6 in use.

In use the results obtained by means of the present invention permit the production of products such as disposable diapers having less contact with the wearer's skin surface with the results of reducing incidences of diaper rash and promoting flow of liquid into the absorbent layer. Similarly in products such as incontinent pads and feminine napkins, these results may be obtained. FIGS. 6 and 7 illustrate a disposable diaper incorporating the facing material of the present invention. As shown, diaper 60 includes a backing 62 of impervious material such as polyethylene film, absorbent layer 64 of material such as creped wadding, cellulose fluff, or the like, and the facing material 66 of the present invention. The materials may be integrated as by bonding with adhesive lines which may also be placed in other locations if desired. The construction and fabrication of disposable diapers is well-known and described in numerous patents such as, for example, Endres U.S. Pat. No. 3,848,595 and Eckert U.S. Pat. No. 3,774,610.

Thus it is apparent that there has been provided, in accordance with the invention, a lightweight nonwoven fabric and method of producing it that fully satisfy the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. Nonwoven web having a basis weight in the range of from 0.4 oz/yd$^2$ to 2.0 oz/yd$^2$ and density in the range of from 0.08 to 0.20 g/cc comprising randomly oriented thermoplastic filaments overlapping and bonded with a fine pattern of fused bond areas covering 5 to 50% of the web surface with a frequency of 50 to 3200 bond areas per square inch and individual bond area in the range of 0.0005 to 0.0015 in$^2$, said web also containing a gross pattern of embossments covering 5 to 80% of the web surface with a frequency of 1 to 500 embossments per square inch and individual embossment area in the range of 0.003 to 0.03 in$^2$ resulting in an effective Ames web thickness of at least 0.010 inch.

2. The web of claim 1 wherein said filaments are generally continuous, melt spun polymers selected from the group consisting of polyolefins, polyesters, and polyamides, and mixtures thereof.

3. The web of claim 1 containing up to 70% of cellulose fibers.

4. The web of claim 1 containing up to 5% of a filler material.

5. The web of claim 2 wherein said filaments are generally continuous, melt spun polypropylene.

6. A nonwoven web having a basis weight in the range of from 0.5 to 1.0 oz/yd$^2$ and density in the range of from 0.10 to 0.18 g/cc comprising randomly oriented, generally continuous polypropylene filaments overlapping and bonded with a fine pattern of fused bond areas covering 5 to 50% of the web surface with a frequency of 125 to 325 bond areas per square inch and individual bond area in the range of from 0.0005 to 0.0015 in$^2$, said web also containing a gross pattern of embossments covering 5 to 30% of the web surface with a frequency in the range of 10 to 100 embossments per square inch and individual embossment area in the range of 0.003 to 0.03 in$^2$, resulting in an effective Ames web thickness of at least 0.010 inch.

7. The web of claim 6 containing up to 30% of cellulose fibers.

8. The web of claim 6 containing up to 2% of a filler material.

9. The web of claim 8 wherein said filler is selected from the group consisting of clays and titanium dioxide.

10. Method of forming a lightweight, bulky nonwoven web comprising the steps of,
    (a) melt spinning a thermoplastic polymer into filaments,
    (b) collecting said filaments into a randomly oriented, overlapping web,
    (c) bonding said web under pressure producing a fine pattern of fused bond areas covering 5 to 50% of the web surface with a frequency of 50 to 3200 bond areas per square inch and individual bond area in the range of 0.0005 to 0.0015 in$^2$, and
    (d) embossing said web under pressure producing a gross pattern of embossments covering 5 to 80% of the web surface with a frequency of 1 to 500 embossments per square inch and individual embossment area in the range of from 0.003 to 0.030 in$^2$.

11. The method of claim 10 wherein said bonds are produced under conditions of 275° F. to 350° F., 3000 to 50,000 psi and 500 to 1500 fpm and said embossments are produced under conditions of 125° F. to 350° F., shimmed spacing of 0.002 to 0.010 inch and 500 to 1500 fpm.

12. The method of claim 10 wherein said thermoplastic polymer is selected from the group consisting of polyolefins, polyesters, and polyamides.

13. The method of claim 12 wherein the polymer is polypropylene.

14. The method of claim 12 including the step of mixing up to 70% cellulose fibers with said thermoplastic fibers in forming said web.

15. The method of claim 12 including the step of mixing up to 5% of a filler material with said thermoplastic fibers in forming said web.

* * * * *